(12) United States Patent
Kokawa et al.

(10) Patent No.: US 6,532,805 B1
(45) Date of Patent: Mar. 18, 2003

(54) MICRO-MATERIAL TESTING APPARATUS

(75) Inventors: Ryohei Kokawa, Kanagawa (JP); Naoya Tada, 5-16, Tsuruyama-cho, 2-chome, Teramachi-dori, Imadegawa-agaru, Kamigyo-ku, Kyoto 602-0802 (JP)

(73) Assignees: Naoya Tada, Kyoto (JP); Shimadzu Corporation, Kyoto (JP)

( * ) Notice: Subject to any disclaimer, the term of this patent is extended or adjusted under 35 U.S.C. 154(b) by 0 days.

(21) Appl. No.: 09/258,282

(22) Filed: Feb. 26, 1999

(30) Foreign Application Priority Data

Mar. 11, 1998 (JP) ............................................. 10-059731

(51) Int. Cl.$^7$ ........................... G01R 31/28; G01R 1/67; G01B 7/34; G01N 25/72
(52) U.S. Cl. ............................. 73/105; 73/783; 73/790; 73/795; 73/854; 250/309; 428/616; 324/762
(58) Field of Search ....................... 73/105, 783, 790, 73/795, 816, 805, 854, 651; 250/492.2, 306; 369/126; 428/616; 324/762; 702/33

(56) References Cited

U.S. PATENT DOCUMENTS

| | | | | |
|---|---|---|---|---|
| 5,345,815 A | * | 9/1994 | Albrecht et al. | 73/105 |
| 5,423,514 A | * | 6/1995 | Albrecht et al. | 73/105 |
| 5,467,642 A | * | 11/1995 | Hosaka et al. | 73/105 |
| 5,475,318 A | * | 12/1995 | Marcus et al. | 324/762 |
| 5,837,345 A | * | 11/1998 | Nishino et al. | 428/141 |
| 5,856,617 A | * | 1/1999 | Gurney et al. | 73/105 |
| 5,856,967 A | * | 1/1999 | Mamin et al. | 369/126 |
| 5,877,497 A | * | 3/1999 | Binnig et al. | 250/306 |
| 5,929,438 A | * | 7/1999 | Suzuki et al. | 250/306 |
| 6,079,255 A | * | 6/2000 | Binnig et al. | 73/105 |
| 6,092,422 A | * | 7/2000 | Binnig et al. | 73/651 |
| 6,249,747 B1 | * | 1/2001 | Binnig et al. | 702/141 |
| 6,245,444 B1 | * | 6/2001 | Marcus et al. | 428/616 |

* cited by examiner

*Primary Examiner*—Daniel S. Larkin
*Assistant Examiner*—David J. Wiggins
(74) *Attorney, Agent, or Firm*—Kanesaka & Takeuchi

(57) ABSTRACT

An atomic force microscope including a cantilever, a transferring device and a displacement detecting device is used for conducting a material test of a test member based on a load amount and a displacement amount. The test member may be fixed to the cantilever or may be entirely replaced with the cantilever. The transferring device, which is normally used for transferring the cantilever or the sample in accordance with a shape of the sample, constitutes a load applying device for applying a load to the test member, and a displacement of the test member is detected by the displacement detecting device. The load applying device can apply slight displacement and load to the test member, so that the material test for the small material can be conducted.

5 Claims, 9 Drawing Sheets

MICRO-MATERIAL TESTING APPARATUS

BACKGROUND OF THE INVENTION AND RELATED ART STATEMENT

The present invention relates to a material testing apparatus, and more particularly, a micro-material testing apparatus which conducts material tests for superfine materials and ultra thin film materials used for semiconductor devices, such as a micro-machine or LSI.

A material testing apparatus for evaluating a material strength applies a load to a test member to displace the same so as to conduct material strength tests, such as tensile test, compression test, bending test and torsion test. In the conventional material testing apparatus, a driving mechanism, such as air pressure, oil pressure, motor solenoid or the like, has been used as load applying means for applying a load.

In the driving means using air pressure, oil pressure, motor, solenoid or the like, which is provided in the conventional material testing apparatus, it is difficult to slightly control a load amount and a displacement amount to be applied. Therefore, it is difficult to apply a minute load and to provide a small displacement, so that the strength of a micro-material can not be measured accurately. Accordingly, it has been a problem that the conventional material testing apparatus is not suitable for a micro-material test.

Also, the test member, which is an object to be measured in the conventional material testing apparatus, is a block member having a certain thickness. Therefore, it has been a problem that the conventional material testing apparatus can not evaluate a peeling strength of a thin film by applying an additional load only to the thin film.

Further, in the conventional material testing apparatus, fixation of the test member is made by a holding mechanism which mechanically holds the test member. Thus, it has been a problem that this mechanical holding mechanism can not hold the test member securely in case the test member is a micro-material.

The present invention has been made to solve the above problems of the conventional apparatus, and an object of the present invention is to provide a micro-material testing apparatus which can measure a strength of a micro-material.

Another object of the present invention is to provide the micro-material testing apparatus as stated above, which can measure a peeling strength of a thin film material.

A further object of the present invention is to provide a method for securely holding a micro-material.

Further objects and advantages of the invention will be apparent from the following description of the invention.

SUMMARY OF THE INVENTION

To achieve the above objects, the present invention provides a micro-material testing apparatus which conducts a strength test of the micro-material, and the present invention also provides a method for securely holding the micro-material. A mechanism, which is provided in an atomic force microscope and is designed to move a probe for a small amount in order to measure a shape, is diverted as means for slightly moving a micro-material for a material test and applying a minute load thereto. The atomic force microscope is known and is disclosed in, for example, U.S. Pat. No. 4,724,318, RE 33,387 and Japanese Patent Publication (KOKOKU) 7-54249.

The micro-material testing apparatus of the present invention has two embodiments in accordance with variations of applying minute displacement and a minute load to a micro-material, and also has an embodiment in case a micro-material is a thin film.

A first embodiment of the micro-material testing apparatus is formed such that in a cantilever, moving means and displacement detecting means, which are provided in an atomic force microscope, a test member is provided instead of the cantilever, the moving means is used as load applying means for applying a load to the test member, and the displacement detecting means detects a displacement of the test member, so that a material test for the test member is conducted based on a load amount and a displacement amount.

The first embodiment of the micro-material testing apparatus has a structure such that the test member is attached instead of the cantilever in the atomic force microscope, and a sample to be placed in the microscope is used as a sample table. Then, the moving means, which is normally used for moving the cantilever or the sample in accordance with a shape of the sample, is used as load applying means for applying the load to the test member. Thus, the minute displacement or load can be applied to the test member.

Also, a second embodiment of the micro-material testing apparatus is formed such that in a cantilever, moving means and displacement detecting means, which are provided in an atomic force microscope, the moving means and the cantilever constitute load applying means for applying a load to the test member, and displacement of the test member is detected by the displacement detecting means, so that a material test for the test member is conducted based on the load amount and the displacement amount.

The second embodiment of the micro-material testing apparatus has a structure such that a portion of the cantilever in the atomic force microscope constitutes a member for applying the load to the test member, and the moving means, which is normally used for moving the cantilever or the sample in accordance with the shape of the sample, is used as load applying means for applying a load to the test member. Therefore, minute displacement or load can be applied to the test member.

Further, a third embodiment of the micro-material testing apparatus is formed such that in a cantilever, moving means and displacement detecting means, which are provided in an atomic force microscope, the moving means and the cantilever constitute load applying means for applying a load to a thin film test member, and displacement of the test member is detected by the displacement detecting means, so that a peeling test for the thin film test member is conducted based on the load amount and the displacement amount.

The third embodiment of the micro-material testing apparatus has a structure such that a portion of the cantilever in the atomic force microscope constitutes a member for providing a tension to the thin film test member, and the moving means, which is normally used for moving the cantilever or the sample in accordance with a shape of the sample, is used as load applying means for providing the tension to the thin film test member. Therefore, minute displacement or load in a tensile direction can be applied to the thin film test member.

Incidentally, the moving means of the present invention has a mechanism which relatively changes the positions of the sample and the cantilever in the atomic force microscope, and for example, it may be a three-dimensional actuator using a piezoelectric element.

The displacement amount of the test member can be measured by the displacement detecting means. The amount of the load applied to the test member is assumed from the displacement amount and modulus of longitudinal elasticity so that breaking strength of the micro-material can be evaluated. Also, in case the load applying means is formed of the three-dimensional actuator using the piezoelectric element, by determining in advance a relationship between an applied voltage and a load to be generated, the applied load can be assumed from the applied voltage.

Also, by using the measured displacement amount, stress inside the test member can be evaluated by employing a beam theory or a finite element method.

The micro-material testing apparatus can conduct various kinds of tests, such as tensile test, compression test, bending test and torsion test depending on a direction of applying a load by the moving means and an arrangement of the test member.

Also, in the micro-material testing apparatus of the present invention, depending on the contents of the material test, it is necessary to fix the cantilever to the micro-material. In this case, according to the present invention, electricity is applied between the cantilever and the micro-material contacting the cantilever, and a portion of the micro-material contacting the cantilever is fused by heat generated by applying electricity, so that the cantilever is fixed to the micro-material by fusion of the portion of the micro-material. Therefore, the micro-material can be fixed stably and securely.

DETAILED DESCRIPTION OF PREFERRED EMBODIMENTS

Hereunder, embodiments of the present invention will be explained with reference to the attached drawings.

Figure 1:
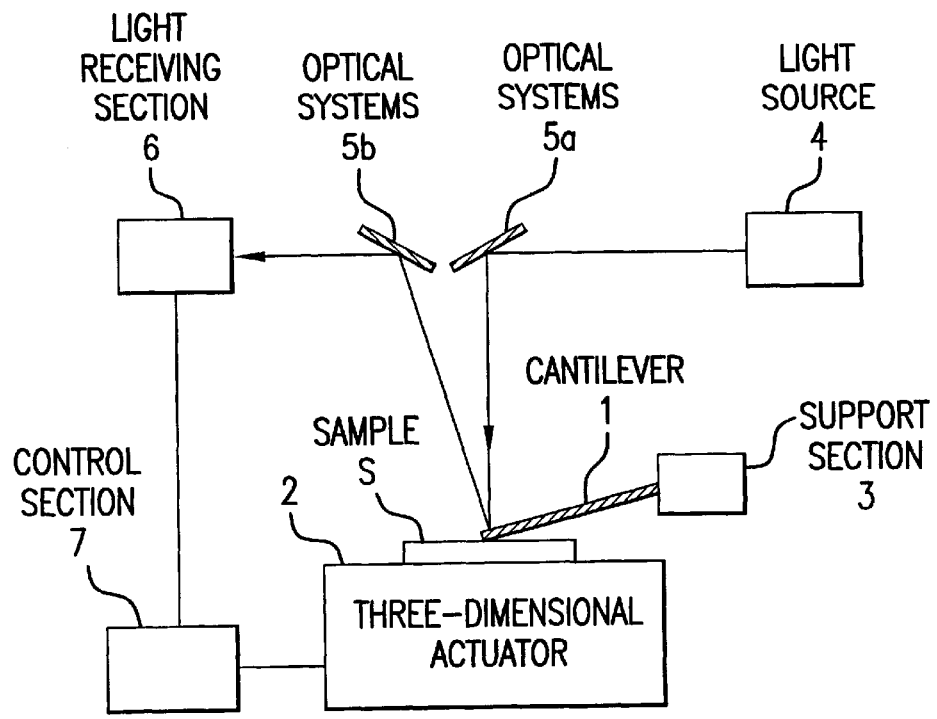
FIG. 1 is a schematic block diagram showing an example of a structure of an atomic force microscope in which a micro-material testing apparatus of the present invention is adopted.

FIG. 1 is a schematic block diagram showing an example of a structure of an atomic force microscope, to which a micro-material testing apparatus of the present invention can be adopted. The atomic force microscope (AFM) includes a probe; a cantilever for supporting the probe; and a displacement measuring system for detecting a bending degree of the cantilever. The atomic force microscope detects an interatomic force (attraction or repulsion) between the probe and a sample, and controls such that the interatomic force is maintained to be constant, to thereby observe a condition of the surface of the sample. In FIG. 1, in the atomic force microscope, a cantilever 1 is opposed to a sample S disposed on a three-dimensional actuator 2, and displacement of the cantilever 1 is detected by a light source 4, optical systems 5a, 5b, a light receiving section 6, and a control section 7.

Figure 2:
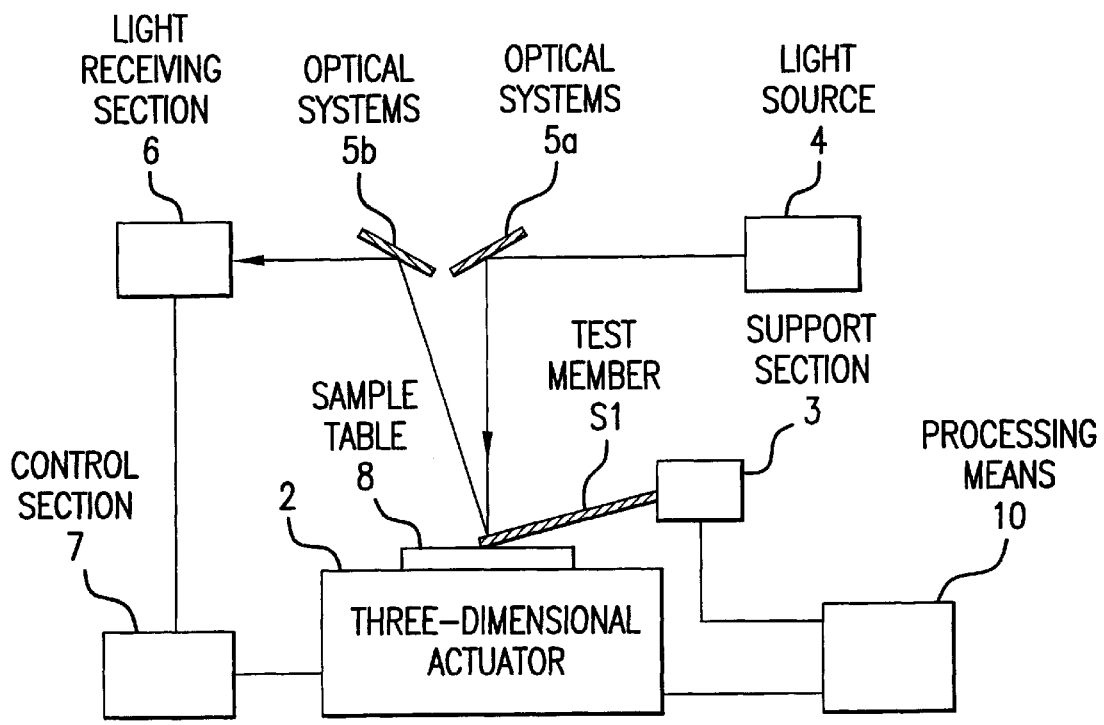
FIG. 2 is an explanatory view schematically showing a first embodiment of the micro-material testing apparatus of the present invention.
Figure 3:
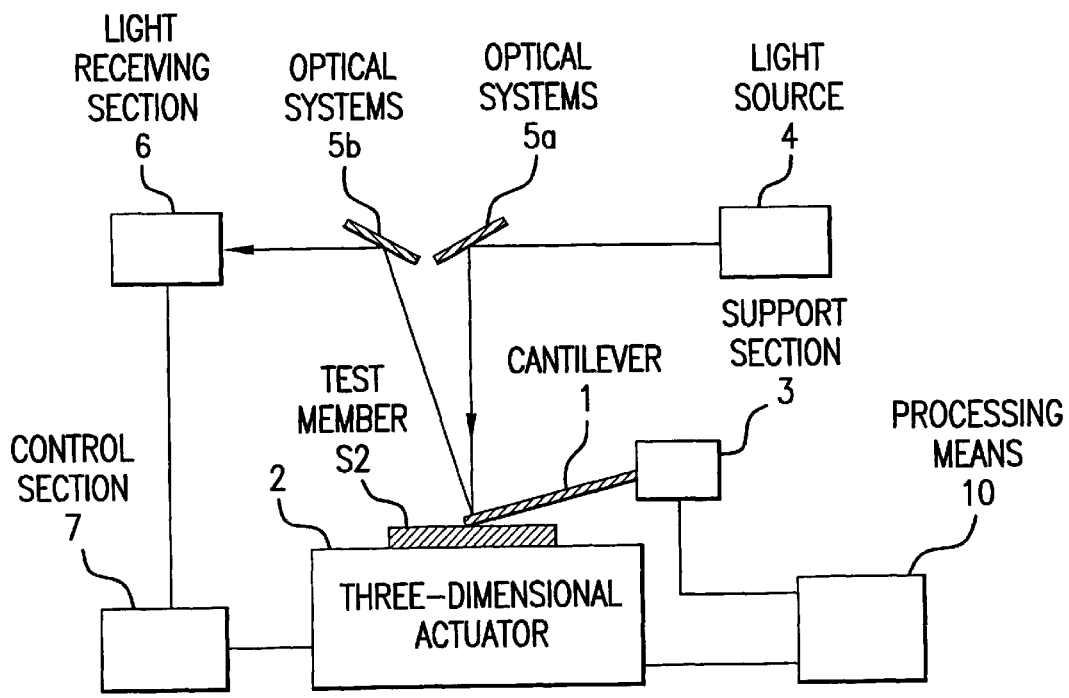
FIG. 3 is an explanatory view schematically showing a second embodiment of the micro-material testing apparatus of the present invention.
Figure 4:
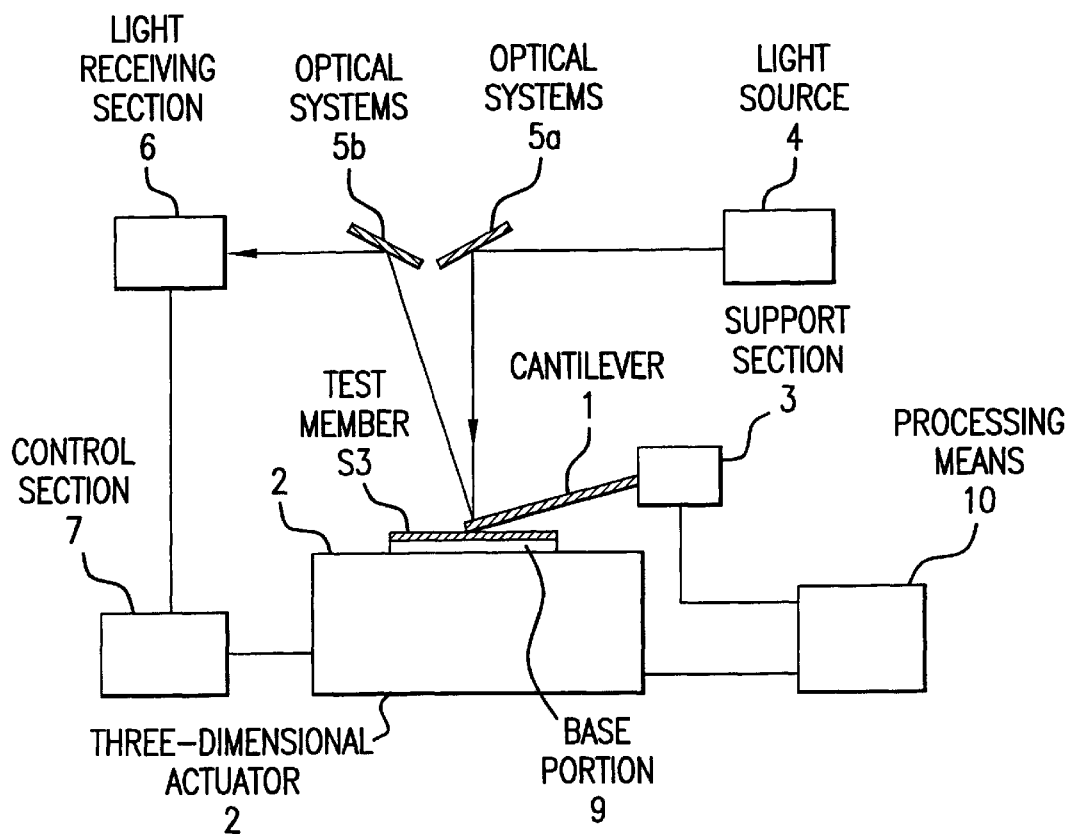
FIG. 4 is an explanatory view schematically showing a third embodiment of the micro-material testing apparatus of the present invention.
Figure 5:
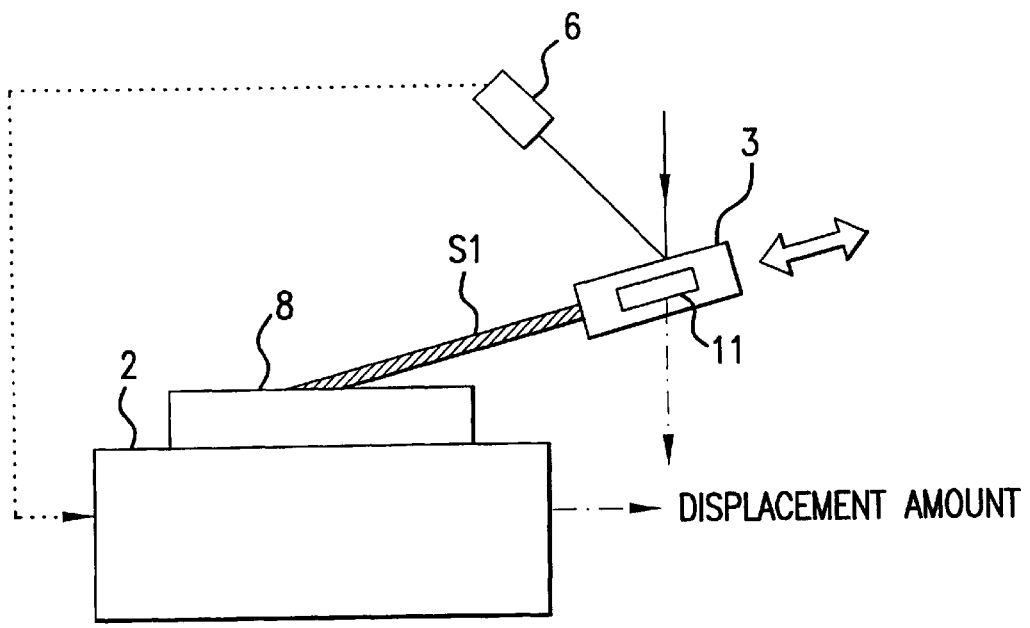
FIG. 5 is a schematic view for explaining the first embodiment of the micro-material testing apparatus of the present invention.
Figure 6:
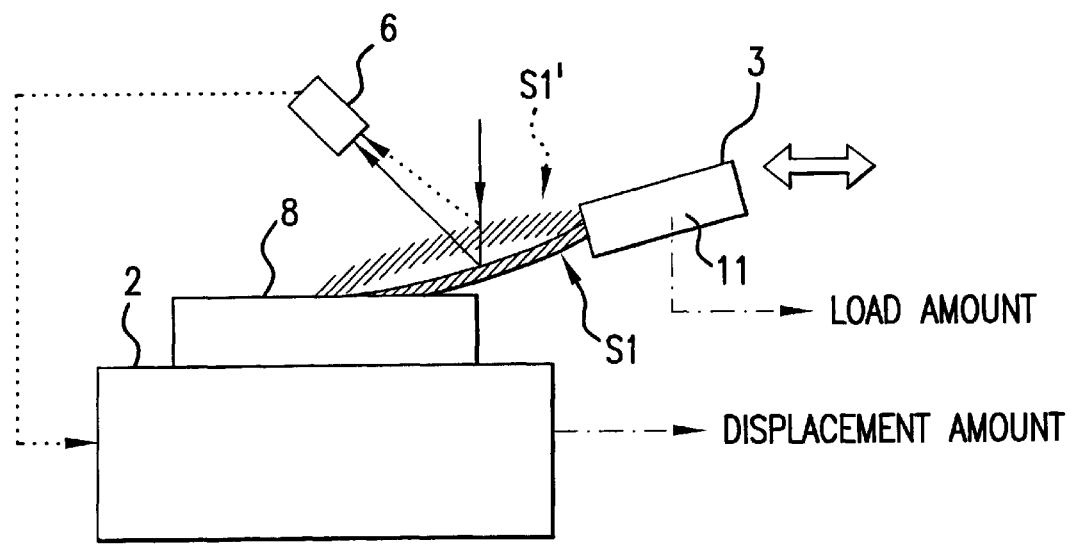
FIG. 6 is a schematic view for explaining the first embodiment of the micro-material testing apparatus of the present invention.
Figure 7:
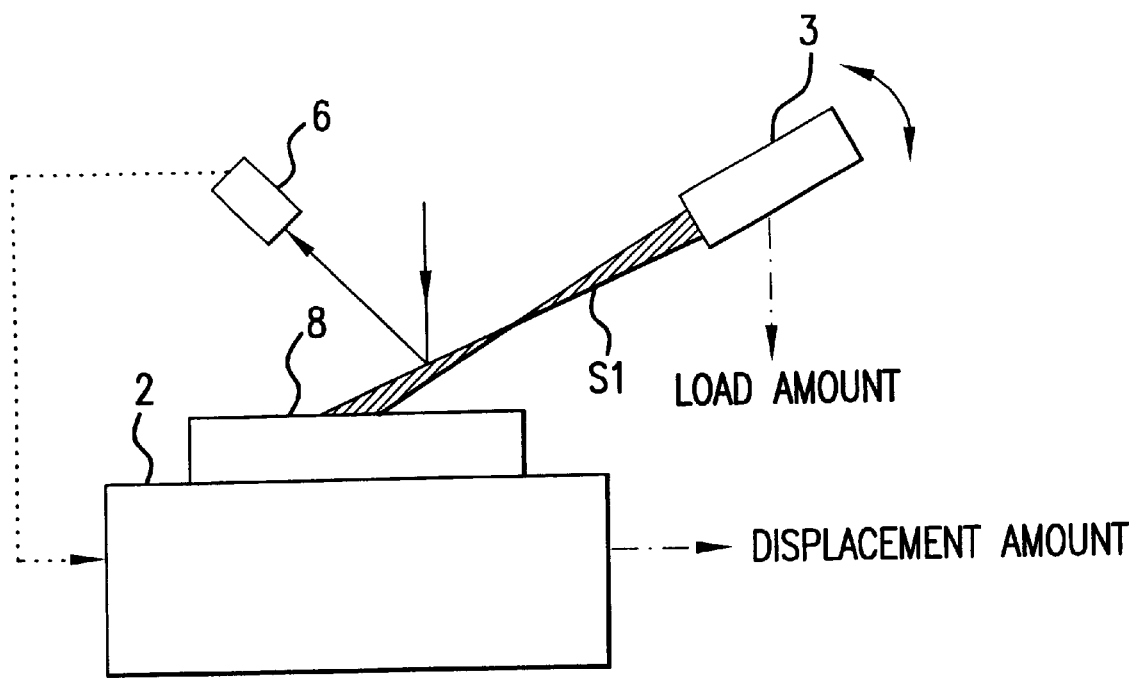
FIG. 7 is a schematic view for explaining the first embodiment of the micro-material testing apparatus of the present invention.
Figure 11A:
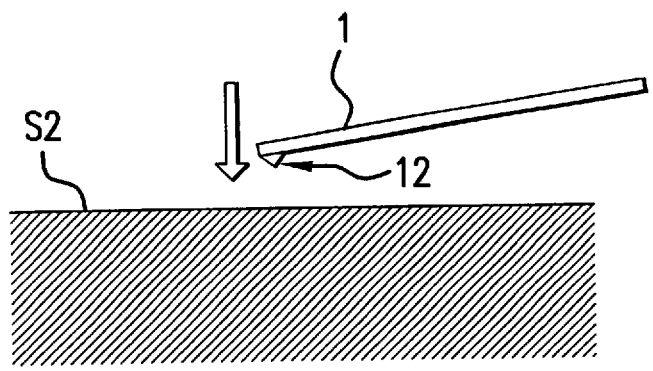
FIGS. 11(a) through 11(c) are schematic views for explaining fixation of a cantilever to the micro-material.
Figure 11B:
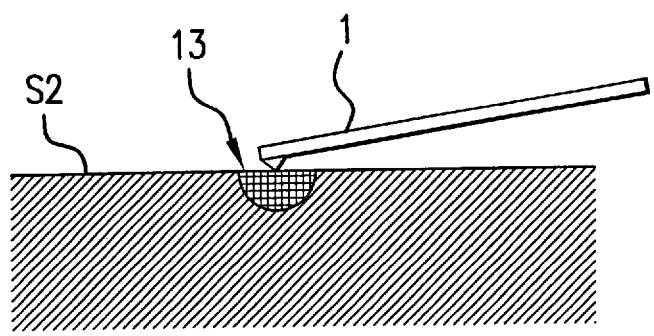
Figure 11C:
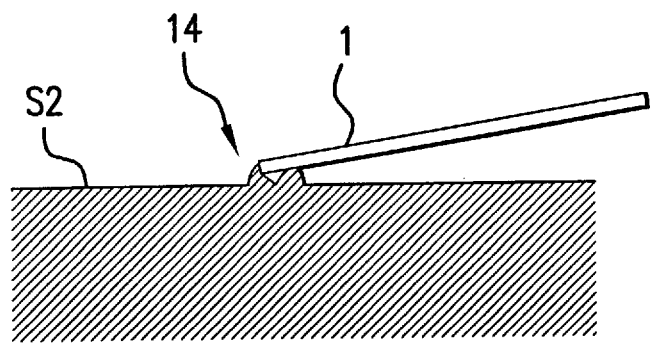
Figure 12:
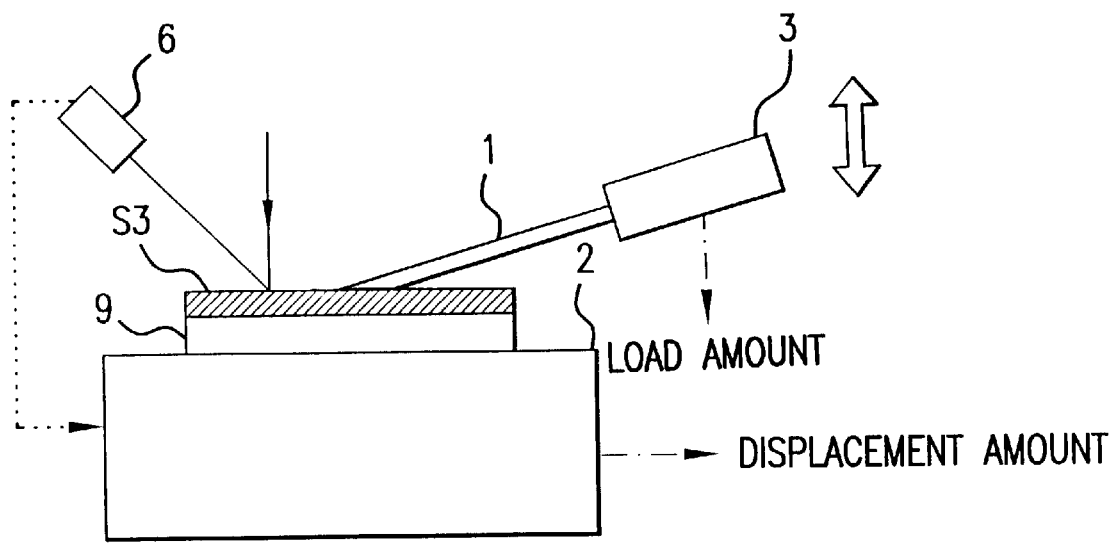
FIG. 12 is a schematic view for explaining the third embodiment of the micro-material testing apparatus of the invention.
Figure 13:
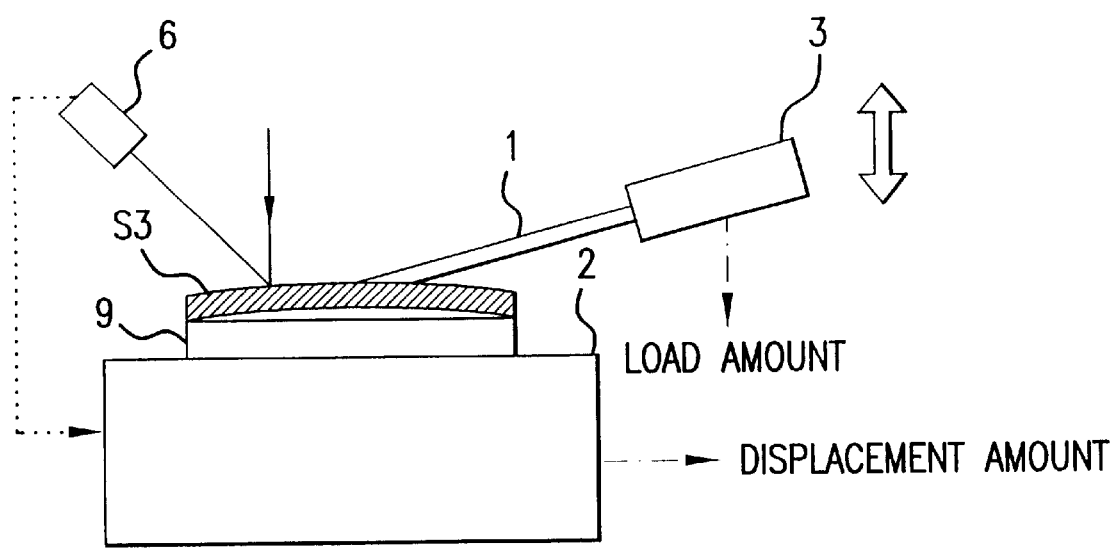
FIG. 13 is a schematic view for explaining the third embodiment of the micro-material of the invention.

Hereinafter, three embodiments of the micro-material testing apparatus of the present invention will be explained with reference to FIGS. 2 through 10(b), FIG. 12 and FIG. 13. More specifically, FIGS. 2 through 4 are views for schematically explaining the three embodiments; FIGS. 5 through 7 are schematic views for explaining the first embodiment; FIGS. 8 through 10(b) are schematic views for explaining the second embodiment; and FIGS. 11 and 12 are schematic views for explaining the third embodiment. Also, FIGS. 11(a) through 11(c) and FIGS. 14(a) through 14(c) are schematic views for explaining fixation of the cantilever to the micro-material.

As shown in FIG. 2, the first embodiment of the micro-material testing apparatus of the invention has a structure such that the cantilever in the atomic force microscope forms a test member S1, and the sample forms a sample table 8. The three-dimensional actuator 2 for supporting the sample table 8 and a support section 3 for supporting the test member S1 form load applying means for applying a load to the test member S1. Also, the light source 4, the optical systems 5a, 5b, the light receiving section 6 and the control section 7 form displacement detecting means.

By applying the load to the testing material S1 by the load applying means, deformation, such as compression, tension, bending and torsion, is caused. The displacement detecting means detects displacement of the test member S1. Processing means 10 obtains, by calculation or the like, a load amount applied by the load applying means, and a displacement amount which is detected by the displacement detecting means.

As shown in FIG. 3, the second embodiment of the micro-material testing apparatus of the invention has a structure such that a portion of the cantilever 1 of the atomic force microscope works as a load applying section with respect to the test member S2. Also, the three-dimensional actuator 2 for supporting the test member S2 and the support section 3 for supporting the cantilever 1 form, together with the cantilever 1, the load applying means for applying the load to the test member S2. Further, the light source 4, the optical systems 5a, 5b, the light receiving section 6, and the control section 7 form the displacement detecting means.

By applying the load to the test member S2 by the load applying means, deformation, such as bending and torsion, is caused. The displacement detecting means detects the displacement of the test member S2. The processing means 10 obtains, by calculation or the like, the load amount applied by the load applying means and the displacement amount detected by the displacement detecting means.

Also, the third embodiment of the micro-material testing apparatus of the invention conducts a peeling test by using a thin film as a test member, and has a structure such that a portion of the cantilever 1 of the atomic force microscope works as a load applying section with respect to a test member S3 as shown in FIG. 4. Also, the three-dimensional actuator 2 and the support section 3 for supporting the cantilever 1 form the load applying means for applying a tensile load to the peeling test member S3. Further, the light source 4, the optical systems 5a, 5b, the light receiving section 6, and the control section 7 form the displacement detecting means.

By applying the tensile load to the peeling test member S3 by the load applying means, a thin film portion is peeled off from a base portion 9. The displacement detecting means observes the displacement of the peeling test member S3 to detect a peeling state. The processing means 10 obtains a peeling strength by calculation or the like based on the load amount applied by the load applying means and the displacement amount detected by the displacement detecting means.

Incidentally, a piezoelectric element may be used as the three-dimensional actuator 2, and a semiconductor laser may be used as the light source 4. Also, a beam splitter, a mirror or a lens system may be used as optical systems 5a, 5b, and a photodiode may be used as the light receiving section 6.

Next, test examples according to the first embodiment will be explained with reference to FIG. 5 through FIG. 7. According to the first embodiment, tests, such as compression test, tension test, bending test, torsion test and creep test; and fatigue tests for these tests, can be carried out.

FIG. 5 shows a case of conducting the compression test and the tension test. In FIG. 5, the cantilever forms the test member S1, and when the three-dimensional actuator 2 or the support section 3 is actuated, the test member S1 is moved toward the sample table 8, or in a direction away from the sample table 8, so that the load is applied to the test member S1 to conduct the compression test or the tension test. Incidentally, in this test, the test member S1 is fixed to the sample table 8 in advance.

The displacement amount of the test member S1 can be obtained by the displacement detecting means shown in FIG. 2, or by a displacement detecting element 11 such as a strain gage disposed in the support section 3.

Also, the load amount applied to the test member S1 is assumed by the displacement amount and modulus of longitudinal elasticity, so that breaking strength of the micro-material can be evaluated. Further, in case the load applying means is formed of the three-dimensional actuator using the piezoelectric element, a relationship between an applied voltage and a generated load is determined in advance, so that the applied load can be assumed from the applied voltage.

Also, by using the measured displacement amount, stress inside the test member can be evaluated by employing a beam theory or a finite element method.

FIG. 6 shows a case of conducting a bending test. In FIG. 6, the cantilever forms the test member S1, and by actuating the three-dimensional actuator 2 or the support section 3, the test member S1 is moved toward the sample table 8 or in a direction away from the sample table 8, so that the load is applied to the test member S1 to conduct the bending test. Incidentally, the test member S1 is fixed to the sample table 8 in advance.

The displacement or bending amount of the test member S1 can be obtained by the displacement detecting means shown in FIG. 2. Also, in case the load applying means is formed of the three-dimensional actuator using the piezoelectric element, the relationship between the applied voltage and the generated load is determined in advance, so that the load amount applied to the test member S1 can be assumed from the applied voltage.

Furthermore, by using the measured displacement amount, stress inside the test member can be evaluated by employing the beam theory or the finite element method.

Incidentally, in the bending test, one of the sides of the test member S1 is compressively deformed, and the other side thereof is torsionally deformed. By measuring the compressive deformation or tensile deformation, the compressive strength or tensile strength can be evaluated.

FIG. 7 shows a case of conducting a torsion test. In FIG. 7, the cantilever forms the test member S1, and by actuating the three-dimensional actuator 2 or the support section 3, the test member S1 is rotated with respect to the sample table 8. Accordingly, a torsional moment is applied in a direction perpendicular to an axial direction of the test member S1, to thereby conduct the torsion test. Incidentally, in the torsion test, the test member S1 is fixed to the sample table 8 in advance.

A displacement or torsion amount of the test member S1 can be obtained by the displacement detecting means shown in FIG. 2. Also, in case the load applying means is formed of the three-dimensional actuator using the piezoelectric element, a relationship between the applied voltage and the generated load is determined in advance, so that an amount of the load applied to the test member S1 can be assumed from the applied voltage.

Further, by using the measured displacement amount, stress inside the test member can be evaluated by employing the beam theory or the finite element method.

Next, test examples according to the second embodiment will be explained with reference to FIG. 8 through FIG. 10(b). According to the second embodiment, tests, such as bending test, torsion test and creep test; and fatigue tests for these tests, can be conducted.

Figure 8:
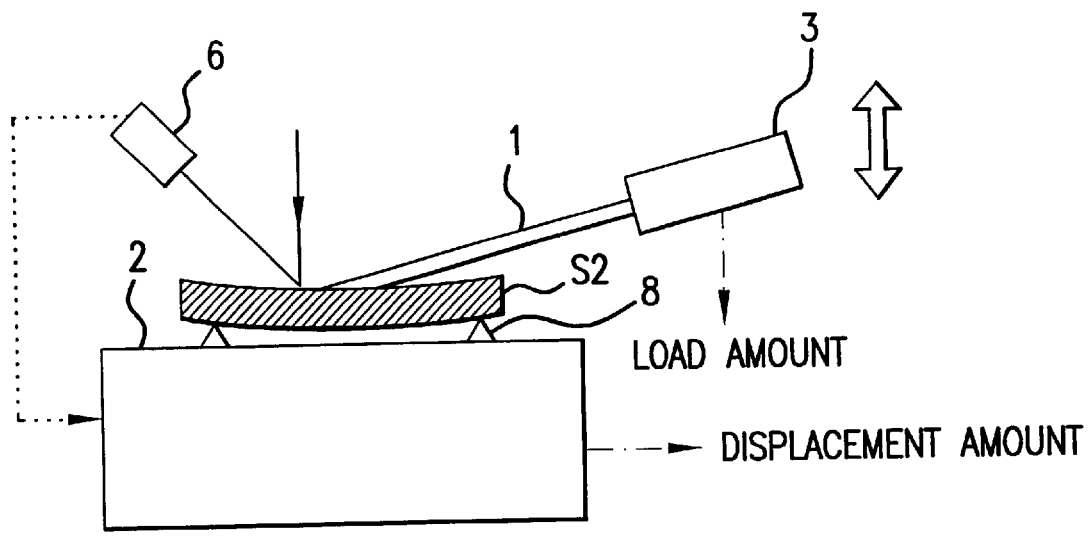
FIG. 8 is a schematic view for explaining the second embodiment of the micro-material testing apparatus of the present invention.

FIG. 8 shows a case of conducting a bending test. In FIG. 8, the test member S2 is supported on the three-dimensional actuator 2, and the cantilever 1 abuts against the test member S2. In this state, the three-dimensional actuator 2 or the support section 3 is actuated such that the cantilever 1 pushes down the test member S2 toward the sample table 8. Alternatively, under the condition that the cantilever 1 and the sample table 8 are fixed to the test member 52, the cantilever 1 is moved in a direction away from the sample table 8. Accordingly, a load is applied to the test member S2 to bend the same, so that the bending test is conducted.

The displacement or bending amount of the test member S2 can be obtained by the displacement detecting means shown in FIG. 3. Also, in case the load applying means is formed of the three-dimensional actuator using the piezoelectric element, a relationship between the applied voltage and the generated load is determined in advance, so that the amount of the load applied to the test member S2 can be assumed from the applied voltage.

Further, by using the measured displacement amount, stress inside the test member can be evaluated by employing the beam theory or the finite element method.

Figure 9:
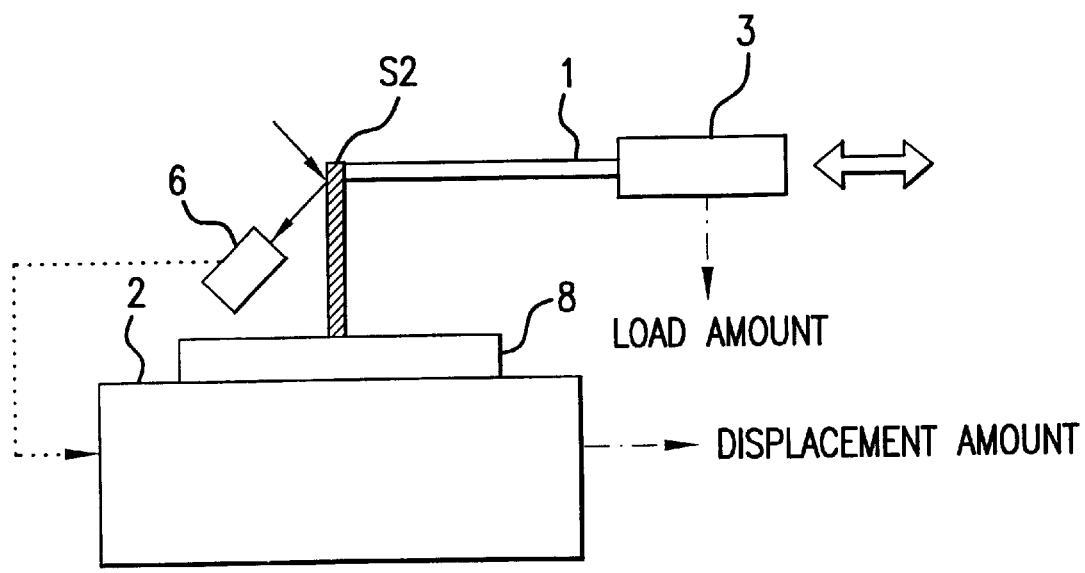
FIG. 9 is a schematic view for explaining the second embodiment of the micro-material testing apparatus of the present invention.

Also, FIG. 9 shows another structure of a bending test. In this example, one end of the test member S2 is fixed to the sample table 8, and the other end thereof is pressed or pulled by the cantilever 1, so as to cause bending deformation. Detections of the displacement amount and load amount can be made as in the example of FIG. 8.

Figure 10A:
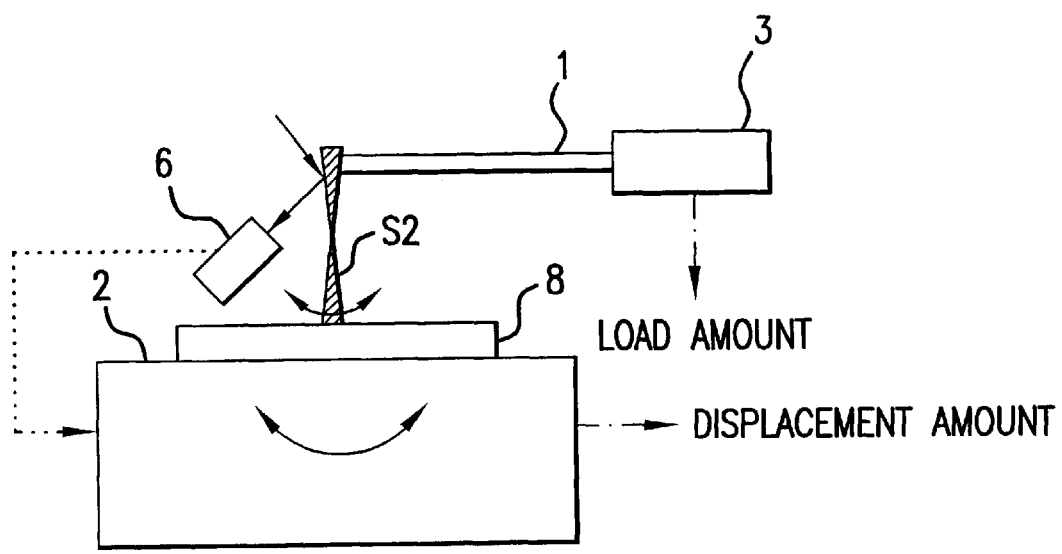
FIGS. 10(a) and 10(b) are schematic views for explaining the second embodiment of the micro-material testing apparatus of the present invention.
Figure 10B:
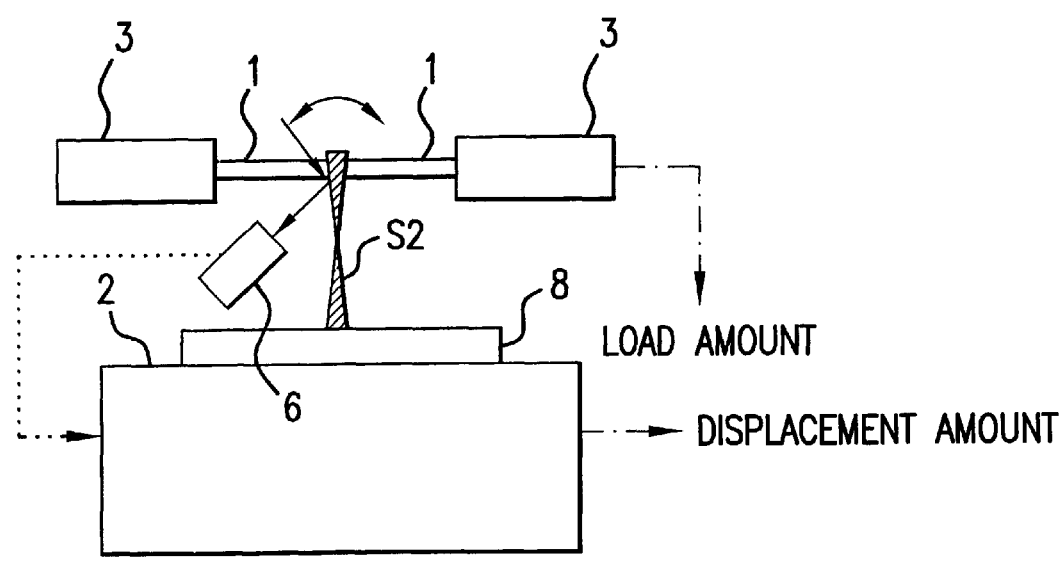

FIGS. 10(a) and 10(b) show a case of conducting a torsion test. In FIG. 10(a), an upper portion of the test member S2 is fixed by means of the support section 3, and by rotationally driving the three-dimensional actuator 2, the test member S2 is rotated with respect to a side of the sample table 8. Accordingly, a load is applied to the test member S2 in a direction perpendicular to the axial direction of the test member S2 to twist the same, to thereby conduct the torsion test. Also, as shown in FIG. 10(b), the upper portion of the test member S2 is fixed by two support sections 3 opposed to each other, and the load is applied to both sides of the test member S2 to apply the torsional moment.

The displacement or torsion amount of the test member S2 can be obtained by the displacement detecting means shown in FIG. 3. Also, in case the load applying means is formed of the three-dimensional actuator using the piezoelectric element, a relationship between the applied voltage and the generated load is determined in advance, so that an amount of the load applied to the test member S2 can be assumed from the applied voltage.

Further, by using the measured displacement amount, stress inside the test member can be evaluated by employing the beam theory or the finite element method.

Next, with reference to FIGS. 11(a) through 11(c), a method for fixing the cantilever to the test member S2 will be explained. In FIG. 11(a), a metal with a low-melting point is used as the test member S2, and a head portion 12 of the cantilever 1 is moved to a surface of the test member S2 to contact therewith. After the head portion 12 contacts the surface of the test member S2, as shown in FIG. 11(b), electricity is applied between the cantilever and the test member S2 to heat a contact portion (designated by numeral 13 in the figure) and to fuse the same. By this fusion, as shown in FIG. 11(c), the head portion 12 of the cantilever 1 is connected to the test member S2 (numeral 14 in the figure).

By this fixation, even if the test member S2 is a micromaterial, excellent fixation can be achieved.

Incidentally, in this fixation, if the test member S2 is preheated and a material having a good wetting property is coated on the head portion 12, more satisfactory fixation can be achieved.

FIGS. 12, 13 and 14(a) through 14(c) show cases of conducting peeling tests for a thin film test member. In FIG. 12, the cantilever 1 is fixed to the test member S3 in which a thin film is formed on the base portion 9, and the three-dimensional actuator 2 or the support section 3 is actuated, so that the test member S3 is moved in the direction away from the actuator 2. As a result, a tensile load is applied to the thin film of the testing material S3 so as to conduct the peeling test.

The displacement amount of the test member S3 is obtained by the displacement detecting means shown in FIG. 4, and in case the load applying means is formed of the three-dimensional actuator using the piezoelectric element, a relationship between the applied voltage and the generated load is determined in advance, so that the amount of the load applied to the test member S3 can be assumed from the applied voltage.

From the change in the displacement amount of the test member S3, it can be detected that the thin film is peeled off. From the load amount at this time, the load at the time of peeling can be detected.

Figure 14A:
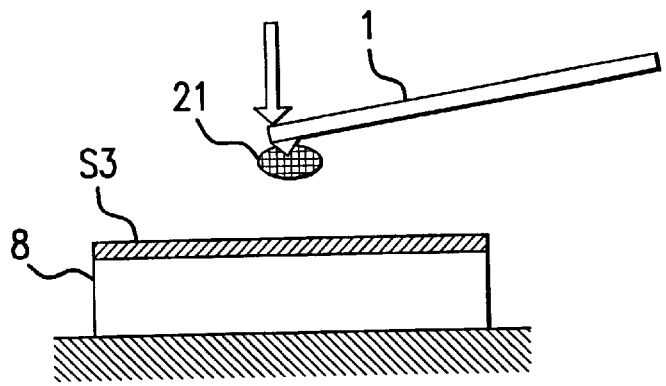
FIGS. 14(a) through 14(c) are schematic views for explaining fixation of the cantilever to the micro-material.
Figure 14B:
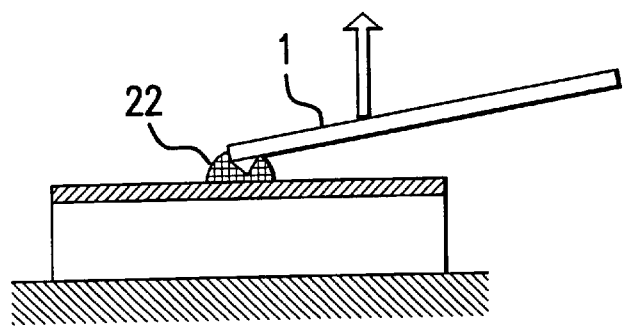
Figure 14C:
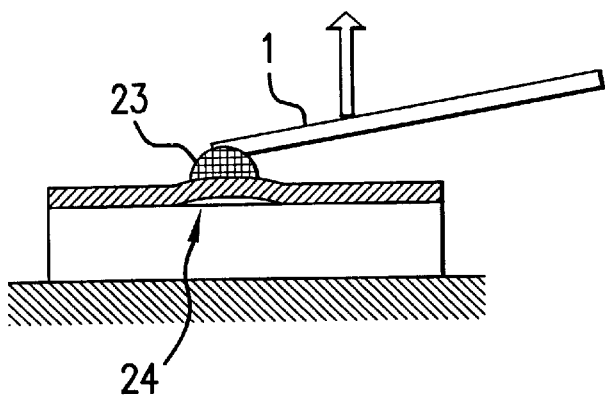

Bonding the cantilever and the test member S3 can be made by using an adhesive. As shown in FIG. 14(a), an adhesive 21 is applied onto the head portion of the cantilever 1, and as shown in FIG. 14(b), the head portion is closely contacted with the thin film portion of the test member S3, to solidify the adhesive (designated by numeral 22 in the figure). After this bonding, as shown in FIG. 14(c), the cantilever 1 is moved to conduct the peeling test. When the thin film is peeled off to form a peeling portion 24, a rapid displacement is observed, so that the peeling can be detected.

In the respective embodiments, by repeatedly applying the load, fatigue tests thereof can be carried out.

According to the embodiments of the present invention, the structure that the atomic force microscope has can be diverted. Also, a small material testing apparatus which can be used widely can be achieved.

As described above, according to the micro-material testing apparatus of the invention, the strength of the micro-material can be measured. Also, the peeling strength of the thin film material can be measured. Furthermore, according to the method of fixing the micro-material of the invention, the micro-material can be held securely.

While the invention has been explained with reference to the specific embodiments of the invention, the explanation is illustrative and the invention is limited only by the appended claims.

What is claimed is:

1. A micro-material testing apparatus for conducting a peeling test, comprising an atomic force microscope provided with a cantilever, transferring means situated adjacent to the cantilever to move a sample, and displacement detecting means for detecting displacement of the sample, wherein a test member includes a base portion and a thin film fixed to the base portion; said test member is held between the cantilever and the transferring means; at least one of the transferring means and the cantilever constitutes load applying means for applying a load to the test member to conduct a thin film peeling test of the test member; and said displacement detecting means detects a peeling of the test member so that the peeling test is performed based on an amount of the load applied by the load applying means and an amount of the peeling measured by the displacement detecting means when the load is applied.

2. A micro-material testing apparatus according to claim 1, wherein said cantilever includes a support section, and the transferring means is a three-dimensional actuator, said cantilever and three dimensional actuator constituting said load applying means.

3. A micro-material testing apparatus according to claim 2, wherein said displacement detecting means includes a light source for applying light to the test member, an optical system for directing light from the light source to the test member, a light receiving section for receiving light reflected at the test member, and a control section connected to the light receiving section and the three-dimensional actuator for calculating the displacement of the test member.

4. A method for fixing a micro-material into a desired location in a micro-materials testing apparatus comprising the steps of:

contacting a cantilever with a micro-material, applying a current of electricity between the cantilever and the micro-material contacting with the cantilever to generate heat, fusing a portion of the micro-material contacting with the cantilever by the heat generated at the desired location, and affixing the cantilever to the micro-material by said fusing of the portion of the micro-material.

5. A method for fixing a micro-material according to claim 4, wherein said cantilever is covered with a coating with wetting property, and said micro-material is preheated.

* * * * *